United States Patent [19]

Harris et al.

[11] Patent Number: 5,607,847
[45] Date of Patent: Mar. 4, 1997

[54] RECOMBINANT HUMAN ANTI-HUMAN IMMUNODEFICIENCY VIRUS ANTIBODY

[75] Inventors: William J. Harris, Carnoustie; Francis J. Carr, Balmedie; Kathryn L. Armour, Aberdeen, all of Great Britain

[73] Assignee: Nissin Shokuhin Kabushiki Kaisha, Osaka, Japan

[21] Appl. No.: 275,053

[22] Filed: Jul. 13, 1994

[30] Foreign Application Priority Data

Aug. 24, 1993 [WO] WIPO ............... PCT/GB93/01798

[51] Int. Cl.⁶ ............ C12P 21/08; C07K 16/10; A01K 39/42; C12N 15/13
[52] U.S. Cl. ............ 435/69.6; 435/172.3; 435/252.33; 530/387.3; 530/388.35; 424/133.1; 424/160.1; 424/148.1
[58] Field of Search ............ 424/133.1, 148.1, 424/154.1, 160.1; 435/70.21, 172.2, 172.3, 240.3, 252.3, 252.33, 69.6, 240.23, 320.1; 530/387.3, 388.35, 390.1, 389.4; 536/23.53

[56] References Cited

U.S. PATENT DOCUMENTS 5,225,539  7/1993  Winter ............... 530/387.3
5,245,015  9/1993  Fung et al. ............ 530/388.35

FOREIGN PATENT DOCUMENTS

US92/07111  8/1992  WIPO .

OTHER PUBLICATIONS

Fahey, J. L. and Schooley R. (1992) Status of immune-–based therapies in HIV infections and AIDS. Clin exp. Immunol. 88 1–5.
Fox, J. L. (1994) No Winners Againsts AIDS. Bio/Technology vol. 12 p. 128.
Ohno, T. et al. (1991). Proc. Natl. Acad. Sciences USA vol. 88 pp. 10726–10729.
Queen, C. et al. (1989) A humanized antibody that binds to the interleukin 2. receptor. Proc. Natl. Acad. Sci. USA. vol. 65 pp. 10029–10033.
Jackson et al., Lancet 2:647–652 (1988).
Winter and Milstein, Nature 349:293–299 (1991).
Emini et al., Nature 355:728–730 (1992).
Riechmann et al., Nature 332:323–327 (1988).

Primary Examiner—Christine M. Nucker
Assistant Examiner—Julie E. Reeves
Attorney, Agent, or Firm—Marshall, O'Toole, Gerstein, Murray & Borun

[57] ABSTRACT

The present invention provides human monoclonal antibodies, derived from the murine mAb NM-01 (PCT/US92/07111), which are specifically reactive with HIV gp120 and have the capacity to neutralize the infection of H9 cells in culture by live HIV-1 strains MN and $III_B$ as shown by reverse transcriptase, p24 and syncytium formation assays. These antibodies were shown to be as or more effective than the parent murine antibody by the aforementioned criteria.

6 Claims, 18 Drawing Sheets

FIGURE 1A

```
                                                        60
CAGATTCAGCTTAAGGAGTCTGGACCTGCTGTCATCAAGCCATCACAGTCACTGTCTCTC
-----+---------+---------+---------+---------+---------+
GTCTAAGTCGAATTCCTCAGACCTGGACGACAGTAGTTCGGTAGTGTCAGTGACAGAGAG

Q  I  Q  L  K  E  S  G  P  A  V  I  K  P  S  Q  S  L  S  L

120
ACCTGCATAGTCTCTGGATTCTCCATCACACAAGTAGTAGTTATTGCTGGCACTGGATCCGC
-----+---------+---------+---------+---------+---------+
TGGACGTATCAGAGACCTAAGAGGTAGTGTGTTCATCATCAATAACGACCGTGACCTAGGCG

```
                                                                    180
CAGCCCCCAGGAAAGGGGTTAGAGTGGATGGGGCGCATATGTTATGAAGGTTCAATAGAC
---------+---------+---------+---------+---------+---------+
GTCGGGGGTCCTTTCCCCAATCTCACCTACCCCGCGTATACAATACTTCCAAGTTATCTG

Q  P  P  G  K  G  L  E  W  M  G  R  I  C  Y  E  G  S  I  D

240
TATAGTCCATCCATCAAAAGCCGGCAGCACCATCTCTCCAGAGACACATCTCTGAAACAGATTC
---------+---------+---------+---------+---------+---------+
ATATCAGGTAGGTAGTTTTCGGCCGTCGTGGTAGAGAGGTCTCTGTGTAGAGACTTGTCTAAG

Y  S  P  S  I  K  S  R  S  T  I  S  R  D  T  S  L  N  R  F
```

```
TTTATCCAGCTGAGTTCTGTGACAAATGAGGACACTGCCATGTATTACTGTTCCAGGGAA
----+----:----+----:----+----:----+----:----+----:----+    300
AAATAGGTCGACTCAAGACACTGTTTACTCCTGTGACGGTACATAATGACAAGGTCCCTT

F  I  Q  L  S  S  V  T  N  E  D  T  A  M  Y  Y  C  S  R  E

AACCATGGTACTACGACCTCTATGGACTACTGGGGTCAAGGAACCTCAGTCACCGTCTCC
----+----:----+----:----+----:----+----:----+----:----+    360
TTGGTACCATGATGCTGGAGATACCTGATGACCCCAGTTCCTTGGAGTCAGTGGCAGAGG

N  H  G  T  T  T  S  M  D  Y  W  G  Q  G  T  S  V  T  V  S

TCA
---:----+    363
AGT

```
GACATTGTGCTGACCCAGTCTCCAGCTTCTTTGGCTGTGTCTCTAGGGCAGAGGGCCACC
----:----+----:----+----:----+----:----+----:----+----:----+   60
CTGTAACACGACTGGGTCAGAGGTCGAAGAAACCGACACAGAGATCCCGTCTCCCGGTGG

D  I  V  L  T  Q  S  P  A  S  L  A  V  S  L  G  Q  R  A  T

ATATCCTGCAGAGCCAGTGAAAGTGTTGATAGTTATGGCAATAGTTTTATGCACTGGTAC
----:----+----:----+----:----+----:----+----:----+----:----+   120
TATAGGACGTCTCGGTCACTTTCACAACTATCAATACCGTTATCAAAATACGTGACCATG

I  S  C  R  A  S  E  S  V  D  S  Y  G  N  S  F  M  H  W  Y
```

```
CAGCAGAAACCAGGACAGTCACCCAAACTCCTCATCTATGTTGCATCCAACCTAGAATCT
----+----.----+----.----+----.----+----.----+----.----+----
GTCGTCTTTGGTCCTGTCAGTGGGTTTGAGGAGTAGATACAACGTAGGTTGGATCTTAGA
                                                          180

Q  Q  K  P  G  Q  S  P  K  L  L  I  Y  V  A  S  N  L  E  S

GGGGTCCCTGCCAGGTTCAGTGGCAGTGGGTCTAGGACAGACTTCACCCTCACCATTGAT
----+----.----+----.----+----.----+----.----+----.----+----
CCCCAGGGACGGTCCAAGTCACCGTCACCCAGATCCTGTCTGAAGTGGGAGTGGTAACTA
                                                          240

```
                                              300
CCTGTGGAGGCTGATGATGCTGCAACCTATTACTGTCAGCAAAATAATGAGGATCCGCTC
---:----+----:----+----:----+----:----+----:----+----:----+
GGACACCTCCGACTACTACGACGTTGGATAATGACAGTCGTTTTATTACTCCTAGGCGAG

P  V  E  A  D  D  A  A  T  Y  Y  C  Q  Q  N  N  E  D  P  L
---:----+----:----+----:----+----:----+----:----+----:----+

333
ACGTTCGGTGCTGGGACCAAGCTGGAGCTGAAAA
---:----+----:----+----:----+----
TGCAAGCCACGACCCTGGTTCGACCTCGACTTT

```
              10v          20v          30v          40v          50v
01MUVH  QIQLKESGPAVIKPSQSLSLTCIVSGFSITSSSYCWHWIRQPPGKGLEWMG
01HUVH  Q:QL:ESGP::::PSQ:LSLTC.VSGFSITSSSYCWHW:RQPPG:GLEW:G
        QVQLQESGPGLVRPSQTLSLTCTVSGFSITSSSYCWHWVRQPPGRGLEWIG
              10^          20^          30^          40^          50^

60v          70v          80v          90v          100v
01MUVH  RICYEGSIDYSPSIKSRSTISRDTSLNRFFIQLSSVTNEDTAMYYCSRENH
01HUVH  RICYEGSIDYSPSIKSR T: RDTS N:F ::LSSVT..DTA:YYC:RENH
        RICYEGSIDYSPSIKSRVTMLRDTSKNQFSLRLSSVTAADTAVYYCARENH
              60^          70^          80^          90^          100^

110v         120v
01MUVH  GTTTSMDYWGQGTSVTVSS
01HUVH  GTTTSMDYWGQG: VTVSS
        GTTTSMDYWGQGSLVTVSS
              110^         120^
```

FIGURE 4B

```
                  10v       20v        30v        40v        50v
01MUVK  DIVLTQSPASLAVSLGQRATISCRASESVDSYGNSFMHWYQQKPGQSPKLL
01HUVK  DI :TQSP:SL: .S:G:R.TI:CRASESVDSYGNSFMHWYQQ.PG:: PKLL
01MUVK  DIQMTQSPSSLSASVGDRVTITCRASESVDSYGNSFMHWYQQTPGKAPKLL
                  10^       20^        30^        40^        50^

60v       70v        80v        90v       100v
01MUVK  IYVASNLESGVPARFSGSGSGSRTDFTLTIDPVEADDAATYYCQQNNEDPLTF
01HUVK  IYVASNLESGVP:RFSGSGS  TD:T:TI .::::D ATYYCQQNNEDPLTF
01MUVK  IYVASNLESGVPSRFSGSGSGTDYTFTISSLQPEDIATYYCQQNNEDPLTF
                  60^       70^        80^        90^       100^

110v
01MUVK  GAGTKLELK
01HUVK  G.GTKL: :
01MUVK  GQGTKLQIT
              110^
```

RECOMBINANT HUMAN ANTI-HUMAN IMMUNODEFICIENCY VIRUS ANTIBODY

FIELD OF THE INVENTION

The present invention is related to the field of molecular biology in general, and the field of humanized antibodies in particular.

BACKGROUND

This application is related to International Patent Application No. PCT/US92/07111, filed on Aug. 24, 1992, which describes materials and methods useful in the prevention and treatment of Human Immunodeficiency Virus (HIV-1) infection and, specifically, monoclonal antibodies useful in passive immunisation of HIV-1 susceptible or infected animals, especially humans. This application gives a background to HIV-1 infection and its prophylactic or therapeutic treatment by passive immunisation, the main points of which are reiterated here.

The infective process of HIV-1 in vivo has been reviewed by McCune Cell, 64 pp. 351–363 (1991). HIV-1 infects cell lineages which express the CD4 receptor. Most of these cells are quiescent, only dividing in response to specific signals, and so HIV-1 infection may cause $CD4^+$ cells to replicate whereupon viral particles are produced, spreading the infection. Since it is inadvisable to stimulate the immune response of an HIV-1 infected animal, it may be that the best way to prevent or treat HIV-1 infection is by passive immunisation. This involves the administration of anti-HIV-1 antibody to the patient, and presumably, it would be desirable for this antibody agent to be non-immunogenic. There is a precedent for such treatment. Human patients suffering advanced acquired immunodeficiency syndrome (AIDS), the syndrome of progressive immune system deterioration associated with HIV-1 infection, were given plasma containing antibodies against HIV-1 and showed a temporary reduction in various disease parameters (Jackson et al., *Lancet*, 2, pp. 647–652, 1988). Also the administration of HIV-1 specific antibody to a chimpanzee, prior to exposure to HIV-1, resulted in the animal remaining free of signs of viral infections (Emini et al., *Nature*, 355, pp. 728–730, 1992).

The HIV-1 major external envelope glycoprotein, gp120, binds to cellular CD4 receptor and facilitates the internalisation of the virus. Several epitopes of gp120 have been associated with the development of neutralizing antibodies with the so-called "principle neutralizing determinant" being localised to the "V3 loop" of gp120, as referenced in the previous Application (PCT/US92/07111). The V3 loop consists of a hypervariable domain which is established by disulphide bonding between cysteine residues flanking the domain.

The PCT Published Patent Application No. PCT/US92/07111 cites examples of antibody reactive to V3 loop which are isolate or type specific and also candidates as broadly neutralizing antibodies, although none of these were proven to neutralize multiple strains of live HIV-1. The patterns of reactivity shown by these antibodies are likely to be related to the array of primary sequences and conformations of the V3 loop. The aforementioned Application also highlights potential inadequacies of such antibodies: CD4 may not be the only cellular receptor responsible for viral infectivity (Cheng-Mayer et al., *Proc. Natl. Acad. Sci. U.S.A.*, 84, pp. 3526–3530, 1987) and antibody/HIV-1 complexes may enhance virus replication by, for example, promoting the infection of monocytes via receptor-mediated endocytosis (Takeda et al., *Science*, 242, pp. 580–583, 1988).

Previous work had shown that certain animal viruses are inactivated by complement, particularly C1q, through an antibody-independent mechanism (see, for example Weiss, in *Molecular Biology of Tumour Viruses, RNA Tumour Viruses*, Weiss et al., Eds., Cold Spring harbour Laboratory, New York, pp. 1219–1220, 1982). While Banapour et al., *Virology*, 252 pp. 268–271 (1986) describe unheated serum preparation as having no effect on the density of HIV-1 or its ability to infect peripheral blood mononuclear cells, Spear et al., *J. Virol.*, 64, pp. 5869–5873 (1990) report that HIV-1 treated with a combination of complement and pooled sera from HIV-1 sero-positive patients exhibits reduced infectivity.

Thus the background to the previous invention (PCT/US92/07111) was the identification of a need for new monoclonal antibody substances which are specifically immunoreactive with HIV-1 and which, preferably, would neutralize multiple HIV-strains. As candidates for use in passive immunisation of infected and non-infected patients, these agents would ideally be able to mediate complement-dependent virolysis of HIV-1 particles and antibody-dependent cytolysis of HIV-1 infected cells.

The aforementioned invention (PCT/US92/07111) provides monoclonal antibodies reactive to the portion of HIV-1 gp120, or the precursor gp160, comprising the amino acid sequence GPGR, characterised by their capacity to neutralize the infection of H9 cells in culture by live HIV-1 strains MN and $III_B$ and to mediate complement-dependent virolysis of HIV-1 particles and/or antibody-dependent cellular cytotoxicity of HIV-1 infected cells. It was suggested that the monoclonal antibodies of the invention would be suitable for use in anti-HIV-1 treatment of animals, especially humans, susceptible to or infected with HIV-1. Within the contemplation of the invention was the similar use of chimeric antibodies, humanized antibodies, antibody fragments or bispecific antibodies, which could be made as derivatives of the antibodies of the invention, and the use of products of the invention in combination with other immunological and/or therapeutic agents.

The invention describes generation of monoclonal antibodies by immunization of a suitable host with live HIV-1, thus presenting gp120 in its native conformation. It is illustrated by the murine monoclonal antibody, NM-01, produced by the hybridoma cell line HB 10726. The efficacy of NM-01 in in vitro assays, the mapping of the epitope of NM-01 to the sequence GPGR of the gp120 V3 loop and the determination of the NM-01 heavy and light chain variable region sequences are described.

It might be expected that a human antibody would be more suitable than a xenogeneic antibody in prophylactic and therapeutic treatment of HIV-1 infection in humans. This is because the human antibody would be less immunogenic than, for example, a murine counterpart (Bruggermann et al., *J Exp Med*, 170, pp. 2153–2157, 1989) and may, depending on the isotype involved, be more efficient at triggering complement-dependent virolysis and antibody-dependent cellular cytotoxicity of HIV-1 infected cells (discussed by Winter and Milstein *Nature*, 349, 293–299, 1991).

To secure the advantages of a human antibody, whilst making use of the antigen-binding properties of an antibody raised in a different species, workers have used the technique of humanization to transfer the antigen-binding loops to a human template (for example Riechmann et al., *Nature*, 332, pp. 323–327, 1988; Tempest et al., *Bio/Technology*, 9, pp.

266–271, 1991). These loops, known as complementarity determining regions (CDRs) are mounted on a scaffold—the frameworks regions—which together make up the so-called variable domains, situated at the N-terminal ends of each antibody chain. Each binding site is formed, in the most part, from three heavy chain and three light chain CDRs, although framework residues can interact with antigen, either directly or indirectly, by altering the CDR conformation. Genes encoding these recombinant antibodies are expressed in, for example, mammalian cells, and their constant region components can be tailored to suit the application.

BRIEF SUMMARY

The present invention provides human monoclonal antibodies, derived from the murine mAb NM-01 (PCT/US92/07111), which are specifically reactive with HIV gp120 and have the capacity to neutralize the infection of H9 cells in culture by live HIV-1 strains MN and $III_B$ as shown by reverse transcriptase, p24 and syncytium formation assays. These antibodies were shown to be as or more effective than the parent murine antibody by the aforementioned criteria.

The monoclonal antibodies according to this invention are especially suitable for use in anti-HIV1 treatment of humans as they are likely to be less immunogenic than xenogeneic antibodies and more effective in complement-dependent virolysis of HIV-1 particles and/or antibody-dependent cellular cytotoxicity of HIV-1 infected cells.

As set forth in the following detailed description, monoclonal antibodies of the present invention were created as human IgG1/K antibodies by humanization of the murine mAb NM-01. The aspects and advantages of the present invention will be apparent upon consideration of the illustrative examples and descriptions of practice of the present invention in the following detailed description thereof, reference being made to the drawings.

BRIEF DESCRIPTION OF THE DRAWINGS

FIGS. 1A, 1B, and 1C show the nucleotide sequence of the murine NM-01 heavy chain variable region (VH) cDNA (SEQ ID NO: 8) and the translation product (SEQ ID NO: 9). The CDRs are boxed.

FIGS. 2A, 2B, and 2C show the nucleotide (SEQ ID NO: 10) and amino acid (SEQ ID NO: 11) sequences of the murine kappa chain variable region (VK cDNA).

In FIG. 4A, the murine NM-01 VH (MuVH) is aligned with its humanized counterpart (HuVH, SEQ ID NO: 13). The indicated framework residues are the murine residues which were incorporated into the humanized chain as discussed in Example 3.

EXAMPLES

Figure 3:
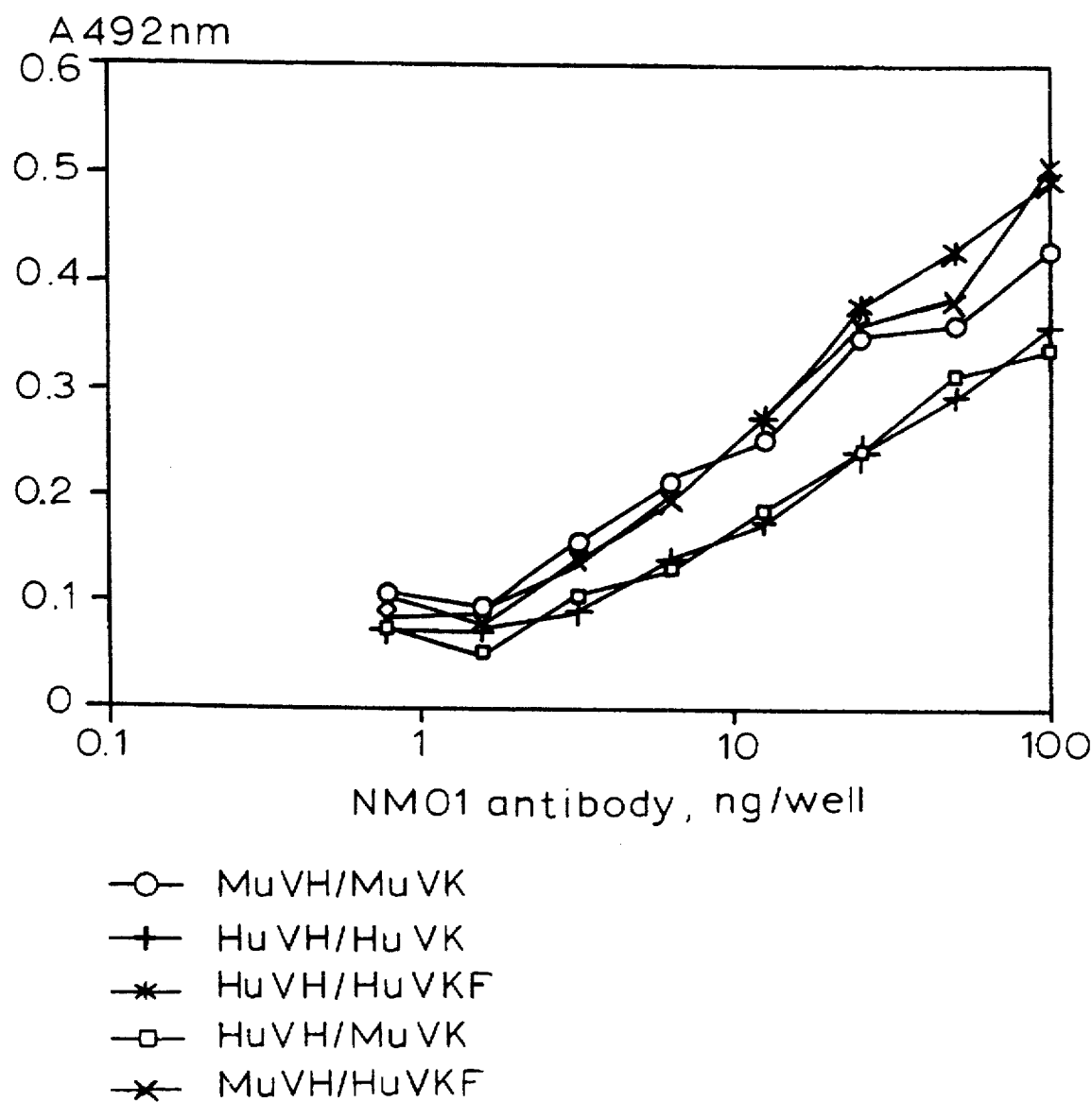
FIG. 3 is a graph showing the ability of various recombinant NM-01 antibodies to bind to recombinant gp120 as judged by ELISA.

The following examples illustrate the practice of the invention in the generation of a humanized monoclonal antibody reactive with HIV-1 gp120. The examples are given for the purpose of illustrating the claimed invention and should not be construed as a limitation of the claimed invention.

More particularly, Example 1 describes the determination of the amino acid sequences of the variable regions of the parent NM-01 murine antibody. Examples 2 and 3 are directed to the generation of chimeric and humanized NM-01 antibodies, Example 4 relates to the characterisation of the epitope of one of the humanized antibodies and Example 5 describes the assessment of the biological activity of this humanized antibody.

Example 1

Isolation of the DNA Sequences Encoding Murine NM-01 Variable Regions

The variable region sequences were disclosed in Application PCT/US92/07111 and were confirmed by independent isolation as described here. The sequences were determined from heavy and light chain cDNAs which were synthesised from cytoplasmic RNA, essentially as described by Tempest et al., loc cit.

1. RNA Isolation

Approximately 200 μg cytoplasmic RNA was isolated from $10^7$ NM-01-producing hybridoma cells by the method of Favalora et al. *Meth Enzymol*, 65, pp. 718–749 (1980). Supernatant obtained from the culture of these cells was assayed for the presence of antibody by solid-phase ELISA using an Inno-Lia mouse monoclonal antibody isotyping kit (Innogenetics, Antwerp, Belgium). The antibody was confirmed to be $IgG_{2b}$/K by this method.

2. cDNA Synthesis

Reverse transcription of NM-01 RNA was initiated from primers based on the 5' end of either the murine $IgG_{2a}$/$IgG_{2b}$ (CG2FOR 5' GGAAGCTAGACCGATGGGGCTGTTGTTTTG3'(SEQ ID NO: 1)) or the murine Kappa (CK2FOR 5' GGAAGCTTGAAGATGGATACAGTTGGTGCAGC3' (SEQ ID NO: 2)) constant region genes. The reactions consisted of 5 μg RNA, 0.5 μM CG2FOR or CK2FOR, 250 μM each dATP, dCTP, dGTP and dTTP, 50 mM Tris-HCl pH 8.3, 75 mM KCl, 10 mM DTT, 3 mM $MgCl_2$, 30 units RNase inhibitor (Pharmacia Milton Keynes, United Kingdom) in 50 μg total volume. Samples were heated at 70° C. for 10 min and then cooled to 37° C. over 30 min. 100 units M-MLV reverse transcriptase (Life Technologies, Paisley, United Kingdom) was added and the reaction allowed to proceed at 37 °C. for 1 hour.

3. Amplification of VH and VK cDNA

The murine variable region cDNAs were amplified by the PCR (Saiki et al. *Science*, 239, 498-491, 1988) using variable region primers, including those described by Orlandi et al., *Proc. Natl. Acad Sci U.S.A.*, 86, pp. 3833-3837 (1989), and signal sequence primers, derived from those of Jones and Bendig, *Bio/Technology*, 9, 88-89 (1991), as well as the constant region primers which were involved in the first strand cDNA synthesis. Several primers gave successful amplification. These additional primers were based on conserved regions at the 5' end of either murine VH, VH1BACK 5' AGGTSMARCTGCAGSAGTCWGG3' (SEQ ID NO: 3) or murine VK, VK1BACK, 5' GACATTCAGCTGAC-CCAGTCTCCA3' (SEQ ID NO: 4) genes or the 3' end of murine VH genes, VH1FOR, 5' TGAGGAGACGGTGAC-CGTGGTCCCTTGGCCCCAG3' (SEQ ID NO: 5). Other primers were designed from signal sequence genes of murine heavy SH3BACK, 5' TTGTCGACATGATGGTGT-TAAGTCTTCTGTACCG3' (SEQ ID NO: 6) or Kappa, SK5BACK, 5' AAGTCGACATGRRTWTASTCACWCAC-CTSCTRKSGKT3' (SEQ ID NO: 7) chains.

For PCR amplification of the VH, the reactions contained 5 μg RNA/cDNA hybrid, 0.5 μM CG2FOR and 0.5 μM VH1BACK or SH3BACK. For the VK, 5 μg RNA/cDNA hybrid was amplified with 0.5 μM each CK2FOR and VK1BACK or SK5BACK. In addition each reaction contained 250 μM each dATP, dCTP, dGTP and dTTP, 10 mM Tris-HCl pH 8.3, 50 mM KCl, 1.5 mM $MgCl_2$, 0.01% (w/v) gelatin, 0.01 (v/v) Tween 20, 0.01% (v/v) NP-40 and 3 units AmpliTaq (Perkin Elmer Cetus, Beaconsfield, UK). Amplification was over 25 cycles of 94° C., 30s; 50 or 55° C., 30s; 72° C., 45s plus 72° C. 5 min to end. To increase specificity, the product of the VH reaction with CG2FOR and SH3BACK was further amplified using VH1FOR and SH3BACK. The VH product sizes were approximately 400 bp (CG2FOR, VH1BACK) and 440 bp (VH1FOR, SH3BACK) as visualized by agarose gel electrophoresis. The VK products were of about 370 bp (CK2FOR, VK1BACK) and 440 bp (CK2FOR, SK5BACK). These DNAs were purified by electrophoresis on low melting point agarose and Elutip-d column chromatography (Schleider and Schuell, Dassel, Germany).

4. Cloning and Sequencing VH cDNA

General cloning methodology is described in Maniatis et al. *Molecular cloning, a laboratory manual* (Cold Spring Harbor Laboratory, Cold Spring Harbor, New York 1982). Enzymes were obtained from Life Technologies (Paisley, United Kingdom).

The CG2FOR, VH1BACK product was cloned into M13 mp18 and M13mp19 (Pharmacia, Milton Keynes, United Kingdom) using the HindIII and PstI restriction sites incorporated into the PCR primers. Clones were sequenced by the dideoxy method (Sanger et al., *Proc. Natl. Acad. Sci. U.S.A.*, 74 pp. 5463–5467, 1977) using T7 DNA polymerase (Pharmacia, Milton Keynes, United Kingdom).

The majority of clones, of which seven were sequenced for the entire insert, contained an identical complete VH gene by comparison with known sequences and represent both fragment orientations. One clone contained a PCR-induced transition mutation. The only other sequence obtained was unidentified but was not VH-like.

As the sequence at the N-terminus of the VH was dictated by the VH1BACK primer, the product of the VH1FOR and SH3BACK reaction was cloned to identify the genuine residues. The product was cloned using SalI restriction site of SH3BACK and the BamHI site which is internal to the VH fragment. The 5' VH sequence was obtained from two clones. The complete VH nucleotide sequence and the amino acid sequence derived by translation are shown in FIG. 1 (SEQ ID Nos. 8 and 9). The extent of the CDRs indicated were determined as defined by Kabat et al., Sequences of Proteins of Immunological Interest (5th edition), U.S. Department of Health and Human Services (1991). These differ from those shown in Application PCT/US92/07111.

5. Cloning and Sequencing VK cDNA

The primers used in the amplification of VK cDNA also contain restriction sites such that the CK2FOR, VH1BACK product was cloned as HindIII-PvuII fragments and the CK2FOR, SK5BACK product as HindIII-SalI fragments into M13mp18 and M13mp19.

The majority (26/31) of clones sequenced contained the same VK insert, identified by homology with known VK sequences. This was obtained from both PCR products in both orientations. The sequences of 21 clones were read for at least 200 nucleotides and, in the case of 14 clones, for the entire VK. There were four PCR-induced point mutations. Of the other clones obtained most had unidentified inserts but one contained a VK-like sequence which would be non-productive due to the lack of the conserved cysteine residue at Kabat position 23 and a frameshift within the DNA encoding CDR3. The sequence has been obtained from RNA of other hybridoma cells and is believed to originate from the fusion partner.

The NM-01 VK nucleotide sequence, including the genuine 5' residues as obtained from CK2FOR, SK5BACK product, is shown in FIG. 2 together with its amino acid translation product (SEQ ID Nos. 10 and 11). Again the CDRs, by the definition of Kabat et al., *loc. cit*, differ from those indicated in Application PCT/US92/07111.

Example 2

Production of Chimeric NM-01 Antibody

The production of a chimeric antibody, consisting of murine variable and human constant regions, is not necessary to the humanization process but can be useful as its ability to bind antigen can suggest that the correct VH and VK have been cloned from the cDNA of the hybridoma and the antibody can be used as a control in assays to assess the efficacy of the humanized antibodies.

VH and VK inserts were amplified from M13 clones using the oligonucleotides VH1FOR and VH1BACK or VK1FOR (Orlandi et al., loc. cit.), 5'GTTAGATCTCCAGCTTG-GTCCC3' (SEQ ID NO: 12) and VK1BACK so that their transfer to chimeric expression vectors could be facilitated by the included restriction sites. The reaction mixtures contained approx. 100 ng M13 ssDNA, 0.5 μM each primer, 250 μM each dATP, dCTP, dGTP and dTTP, 20 mM Tris-HCl pH8.8, 10 mM KCl, 10 mM $(NH_4)_2SO_4$, 2 mM $MgSO_4$ 0.1% (v/v) Triton X-100 and 1 unit Vent DNA polymerase (New England Biolabs, Beverly, Me. U.S.A.) in 50 μl total volumes. The samples were subjected to 10 cycles of 94° C., 30s; 50° C., 30s; 75° C., 1 min. followed by an additional 5 min. at 75° C. The VH product was digested with PstI and BstEII and cloned into M13VHPCR1 (Orlandi et al., loc. cit.). The VK product was cloned into the PvuII and BclI sites of M13VKPCR1 (Orlandi et al., loc. cit.) as a PvuII-BglII fragment. These manipulations served to place the variable regions behind promoter and signal peptide gene sequences in the correct context for expression but also slightly changed residues at their termini:

| VH | I2 to V; | K5 to Q; | S108 to T |
| VK | V3 to Q; | L106 to I | |

These expression cassettes were sequenced completely to confirm the absence of spurious mutations and were then excised from M13 RF DNA as HindIII-BamHI fragments. Partial BamHI digestion was employed so that full length fragments, not cut at the BamHI sites internal to the VH and VK, could be obtained. The VH fragment was cloned into a derivative of pSVgpt (Orlandi et al., loc. cit.) which contains a human IgG1 constant region gene (Takahashi et al., Cell 29, pp. 671–679, 1982). The VK fragment was cloned into pSVhyg (Orlandi et al., *loc. cit.*), already containing the human kappa constant region gene (Hieter et al., Cell, 22, pp 197–207, 1980).

The vectors were contransfected into the rat myeloma YB2/0 (Kilmartin et al., *J. Cell Biol,* 93, pp. 576–582, 1982 (69), available from the American Type Culture Collection, Rockville, Md., U.S.A.) under Accession No. CRL-1662 as previously described (Tempest et al., loc cit.). Mycophenolic acid resistant clones were screened by ELISA for secretion of human IgG/K antibody. ELISA positive clones were expanded and antibody purified from culture medium by protein A affinity chromatography.

The chimeric antibody, purified from the transfected cells, was tested by ELISA for binding to recombinant gp120 (American BioTechnologies Inc., Cambridge, Me., U.S.A.). gp120 (2 ng/100 µl 15 mM $Na_2CO_3$, 35 mM $NaHCO_3$ pH 9.6 per well) was incubated overnight at 4° C. in Immulon 2 plates (Dynatech). The plates were washed with phosphate buffered saline (PBS)-0.05% Tween 20, blocked with 5% normal goat serum (Life Technologies Paisley, United Kingdom) for 1 h at 37° C. and washed again. Antibodies were added at various concentrations in PBS-0.05% Tween 20 and incubated at 37° C. for 1 h. After washing, HRPO-conjugated goat anti-human kappa chain antibodies (Sera-Lab Limited, Crawley Down, Sussex, England; 40 ng/100 µl PBS - 0.05% Tween 20 per well) were added. After 1 h, the wells were washed and incubated in the presence of o-phenyldiamine until color had developed (5–10 min). absorbance was read at 492 nm.

The results (FIG. 3) showed the chimeric antibody (termed MuVH/MuVK) to be reactive against recombinant gp120.

Example 3

Generation of Humanized NM-01 Antibodies

Humanized variable domains are created by transferring the antigen-binding loops of the parent antibody to human variable region frameworks. The frameworks used in the case of NM-01 were those of NEWH VH (Saul et al., *J. Biol Chem,* 253, pp 585–597, 1978) and REI VK (Epp et al., *Eur. J. Biochem,* 45 pp. 513–524, 1974).

Figure 4:
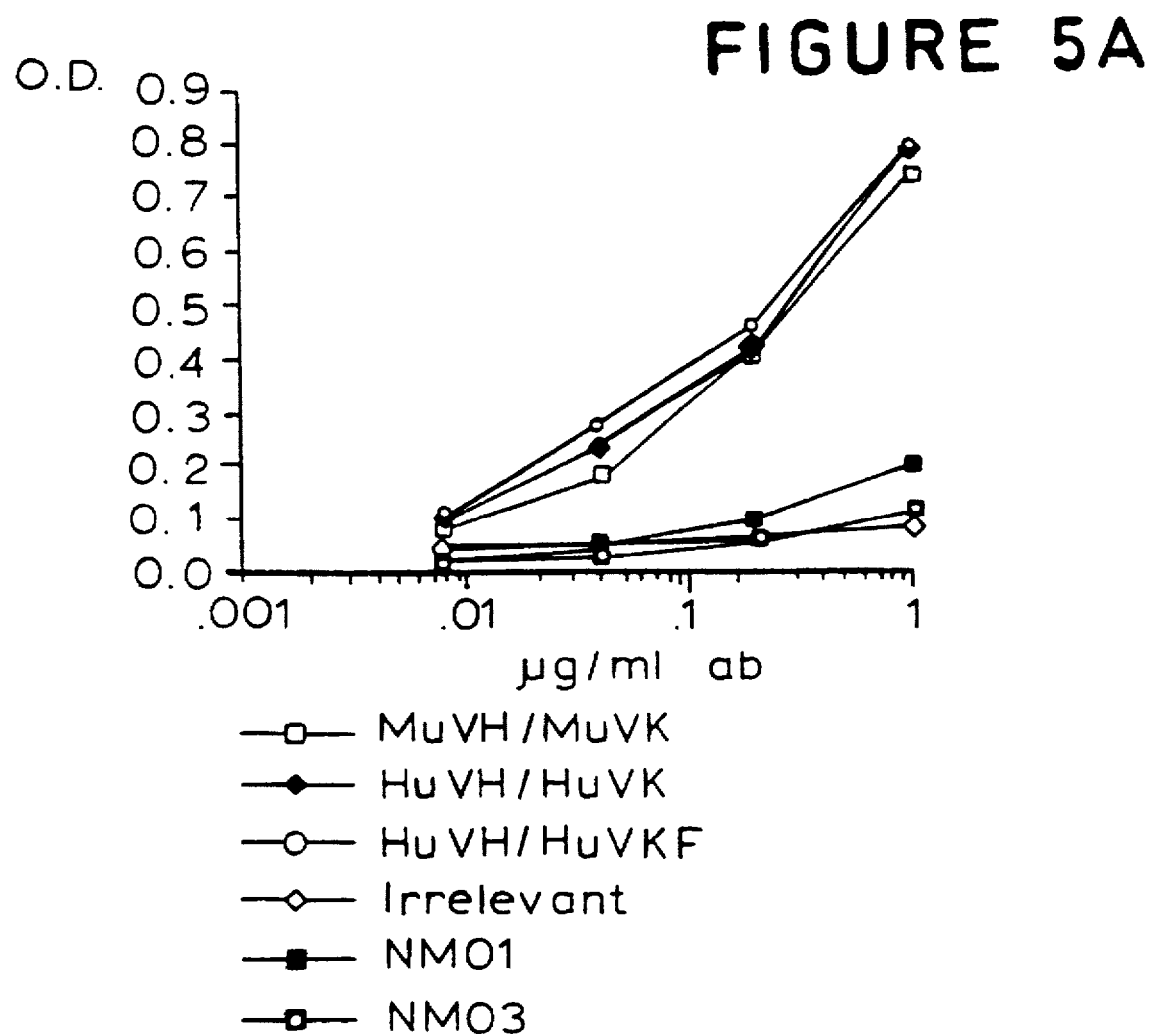
FIGS. 4A and B show two comparisons of amino acid sequences.
In FIG. 4B, the murine NM-01 VK is compared to the humanized NM-01 VK (HuVK, SEQ ID NO: 14). The CDRs are boxed. F71 of the MuVK, which was included in the HuVKF chain, is indicated.

For the humanized heavy chain (HuVH, SEQ ID NO: 13), this involved transfer of the CDRs, as defined by Kabat et al., loc cit., and an additional five residues from the frameworks (FIG. 4A). The four residues prior to CDR1 are not hypervariable and therefore not defined as part of the CDR by Kabat et al., loc cit. but they are part of the loop structure which extends from the β-sheet framework of the domain and thus affect the loop conformation. (Chothia and Lesk, *J Mol. Biol,* 19.6, pp. 901–917, 1987). Residue 71 (Kabat numbering) packs between the loops of CDRs 1 and 2 and is important in determining the conformation of CDR2 (Tramontano et al., *J Mol. Biol,* 215, pp. 175–182, 1990).

The basic humanized VK (HuVK, SEQ ID NO: 14) contained only the CDR sequences of the murine antibody but a second version (HuVKF) additionally included the murine residue, F, at Kabat position 71 (FIG. 4B). The side chain of the amino acid at this position affects the conformation of CDR1 (Chothia and Lesk, loc cit) and reversion to the murine residue has positively affected the binding ability of other humanized antibodies (see, for example, Foote and Winter, *J Mol. Biol,* 224, PP. 487–499, 1992).

DNA encoding the NM-01 CDRs and the aforementioned framework residues was introduced into the appropriate human variable region genes, as contained in derivatives of M13VHPCR1 and M13VKPCR1 (Example 2), by site directed mutagenesis.

The M13 phage were grown in *E. coli.* RZ1032 (dut⁻ ung⁻) to give single-stranded template DNA containing uracil in place of thymine. 0.5 µg DNA was mixed with 1pmol of each mutagenic oligonucleotide and an oligonucleotide which anneals to the M13 template downstream of the insert DNA. The oligonucleotides were annealed to the template in 20 µl of 50 mM Tris-HCl pH7.5, 25 mM $MgCl_2$, 63 mM NaCl by heating to 80° C. for 5 min and cooling slowly to room temperature. dATP, dCTP, dGTP and dTTP were added to 250 µM final concentration, DTT to 7 mM, ATP to 1 mM with 0.5 units T7 DNA polymerase (United States Biochemical Cleveland, Ohio, U.S.A.) and 0.5 units T4 DNA ligase (Life Technologies, Paisley, UK) in the same buffer. The 30 µl reaction was incubated at room temperature at 1h and the DNA ethanol precipated. In order to nick the parental strand, the DNA was dissolved in 50 µl 60 mM Tris HCl pH8.0, 1 mM EDTA, 1 mM DTT, 0.1 mg/ml BSA containing 1 unit uracil DNA glycosylase (Boehringer Mannheim, Lewis, Sussex, UK) and incubated at 37° C., 1h before NaOH was added to 0.2 M and incubation continued at room temperature for 5 min. The DNA was ethanol precipitated, dissolved in 20 µl TE and the insert fragment amplified by PCR. The reaction mixture contained 2 µl mutant DNA, 0.5 µM each M13 forward and reverse primers, 250 µM each of dATP, dCTP, dGTP and dTTP, 10 mM Tris HCl pH8.3, 50 mM KCl, 1.5 mM $MgCl_2$, 0.01% Tween-20, 0.01% gelatin, 0.01% NP40 and 2 units Thermalase (IBI, Cambridge, UK) in 50 µl. Amplification was achieved with 15 cycles of 94° C., 30s; 50° C., 30s; 72° C., 1 min; ending with 72° C, 5 min. The product DNAs were cloned into M13mp19 as HindIII-BamHI fragments. Representative clones were sequenced. The HindIII-BamHI fragments were excised from RF DNA of accurately-mutated clones and transferred to the pSVgpt and pSVhyg expression vectors described in Example 2.

The transfection of YB2/0 and their selection and expression was carried out as in Example 2. HuVH/HuVK F6 (see example 11) is an example of a YB2/0 transfectoma cell line which produces the NM01 HuVH/HuVK antibody. As well as transfections to give humanized antibodies (HuVH/HuVK and HuVH/HuVKF), chimeric and humanized antibody chain expression vectors were co-transfected to give mixed antibodies which would allow the efficacy of the humanized chains to be examined individually.

Figure 5:
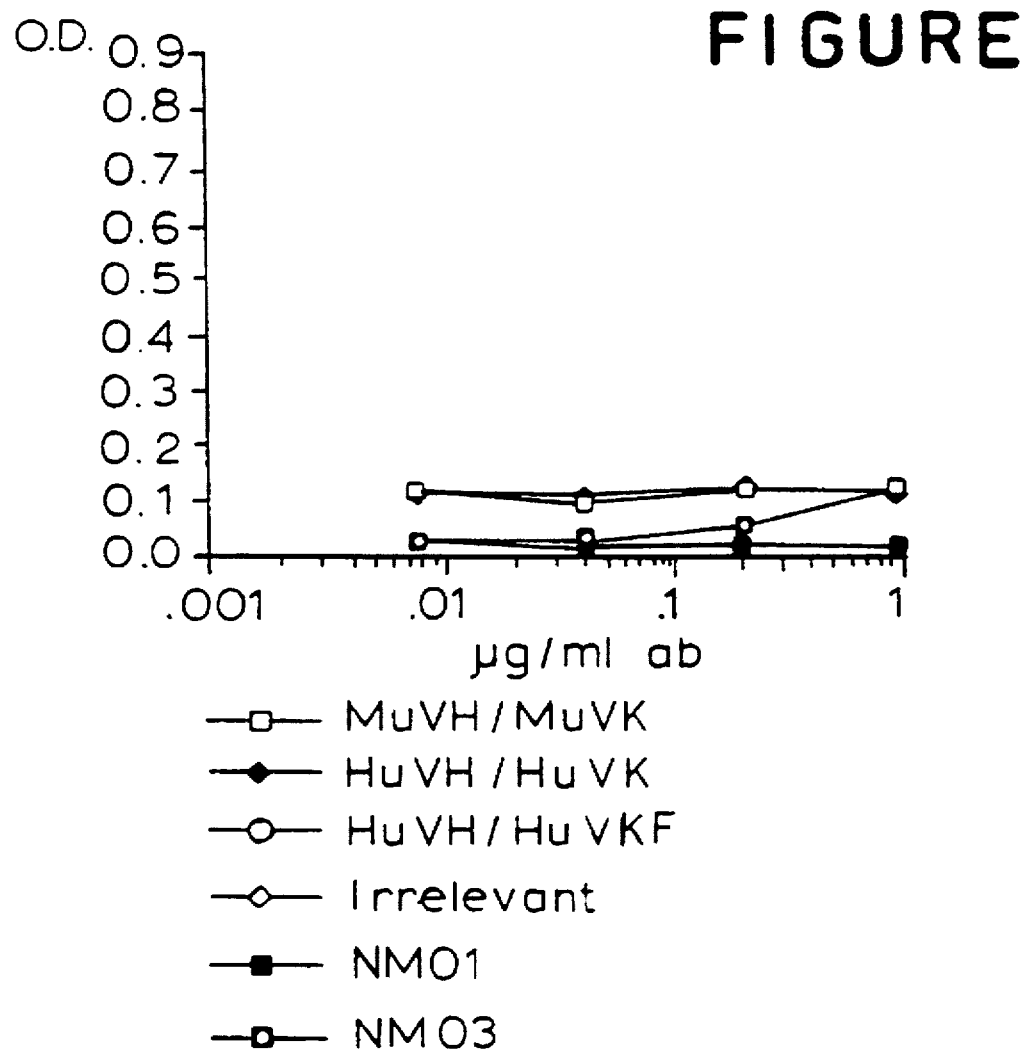
FIG. 5A shows the results of an ELISA measuring the binding of NM-01 antibodies to a lysate of MN virus.
FIG. 5B shows the results of an ELISA measuring the binding of NM-01 antibodies to a lysate of mutant MN virus.
Figure 6:
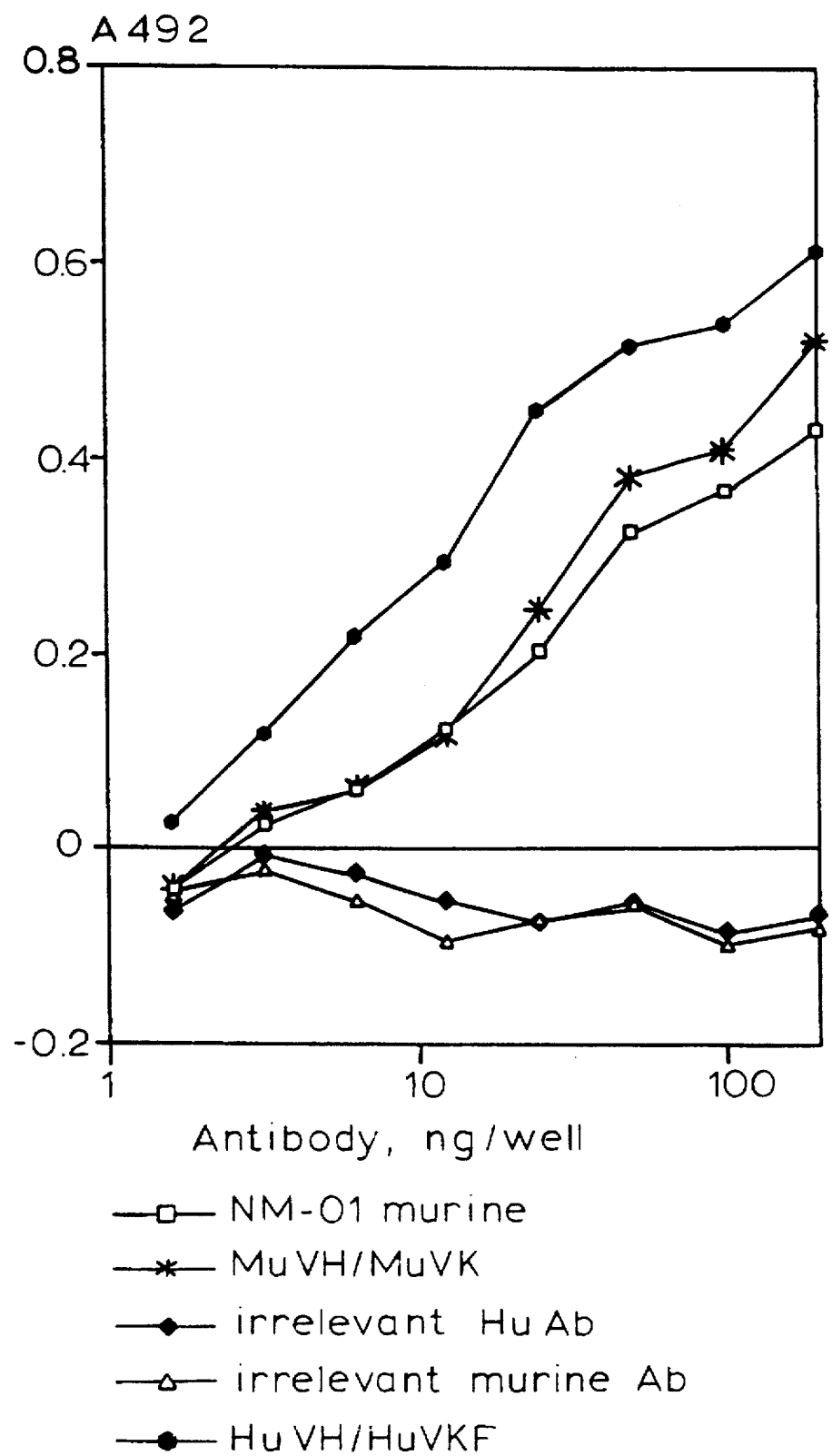
FIG. 6 is a graph depicting the results of an ELISA in which the listed antibodies were tested for their ability to bind to a loop peptide, representing residues 312–326 of HIV-1$_{MN}$gp120.
Figure 7:
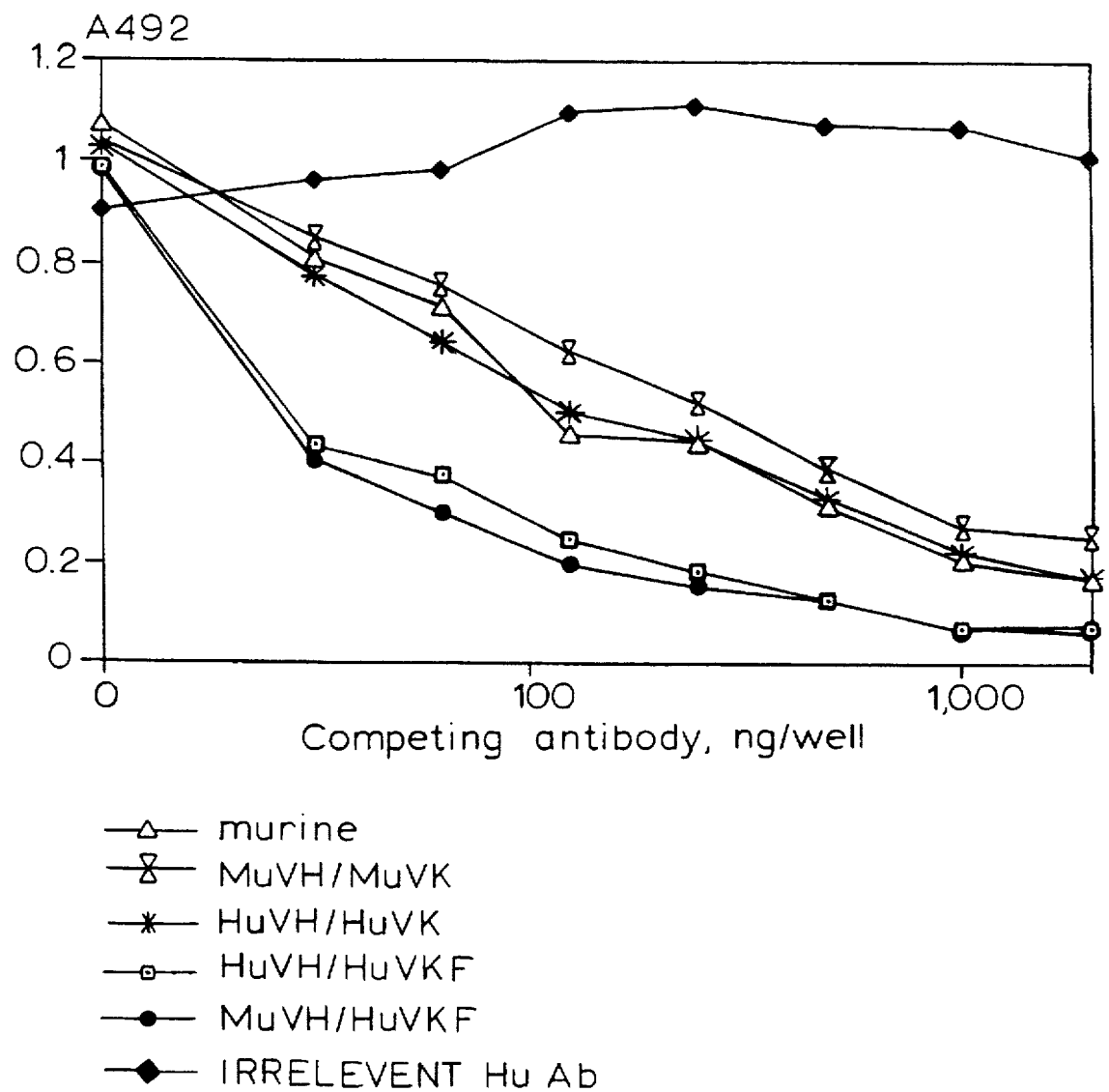
FIG. 7 shows the ability of various NM-01 antibodies to block the binding of labelled murine NM-01 antibody to recombinant gp120.
Figure 8:
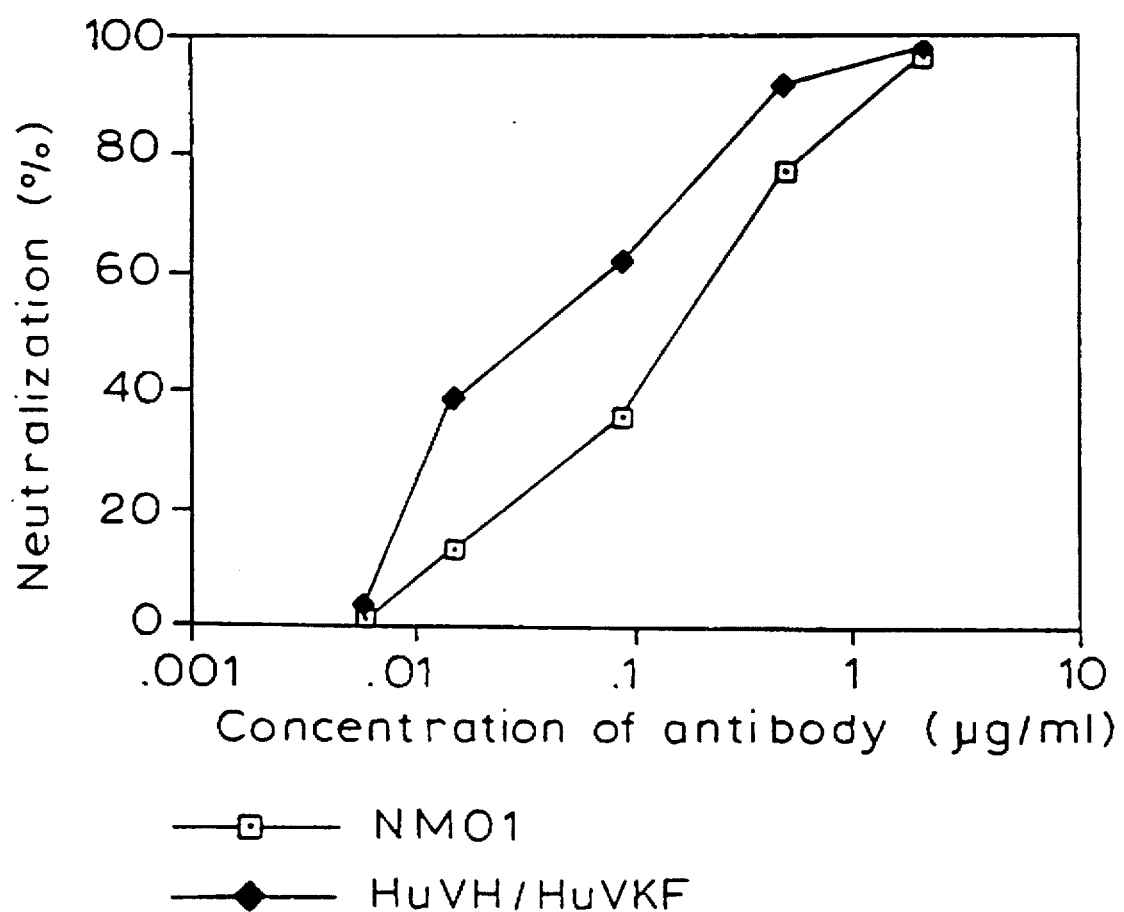
FIGS. 8 and 9 graphically illustrate neutralizing activity of antibodies NM-01 and HuVH/HuVKF against MN and $III_B$ strains of HIV-1 as determined by reverse transcriptase assay.
Figure 9:
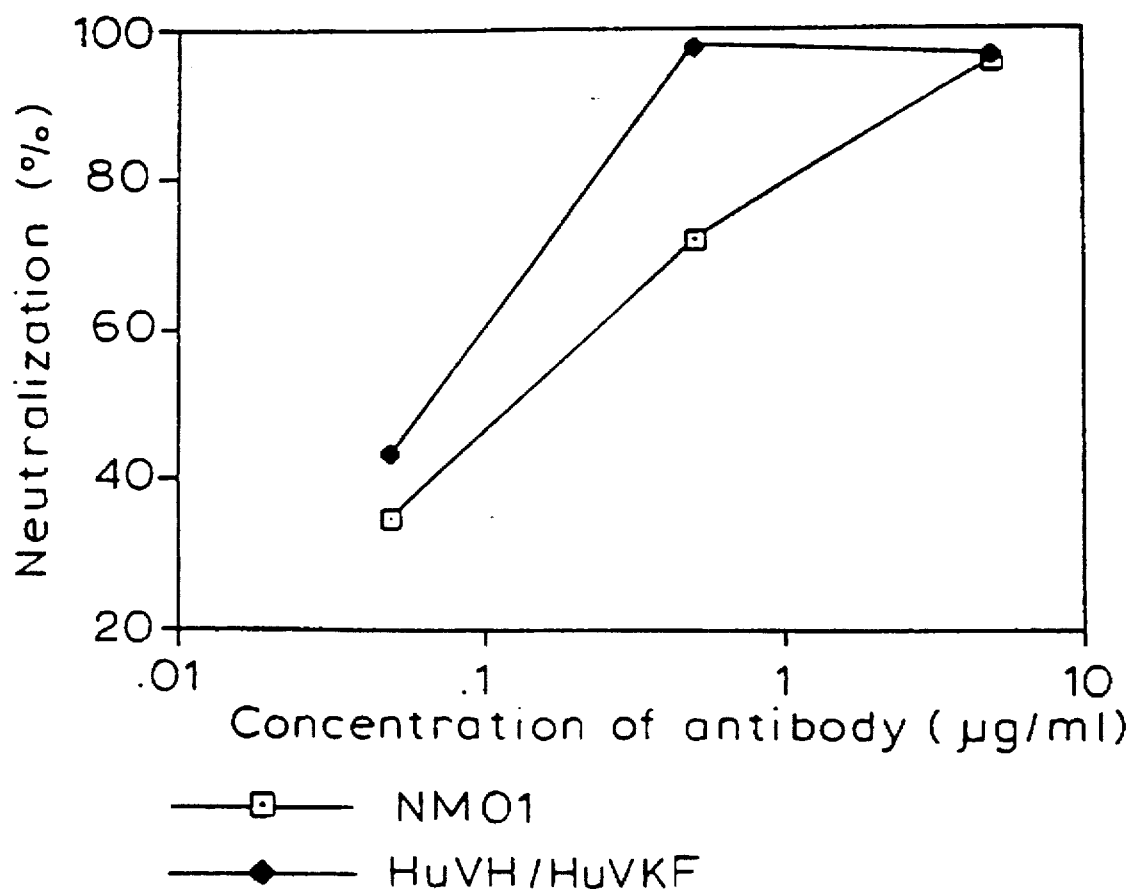
Figure 10:
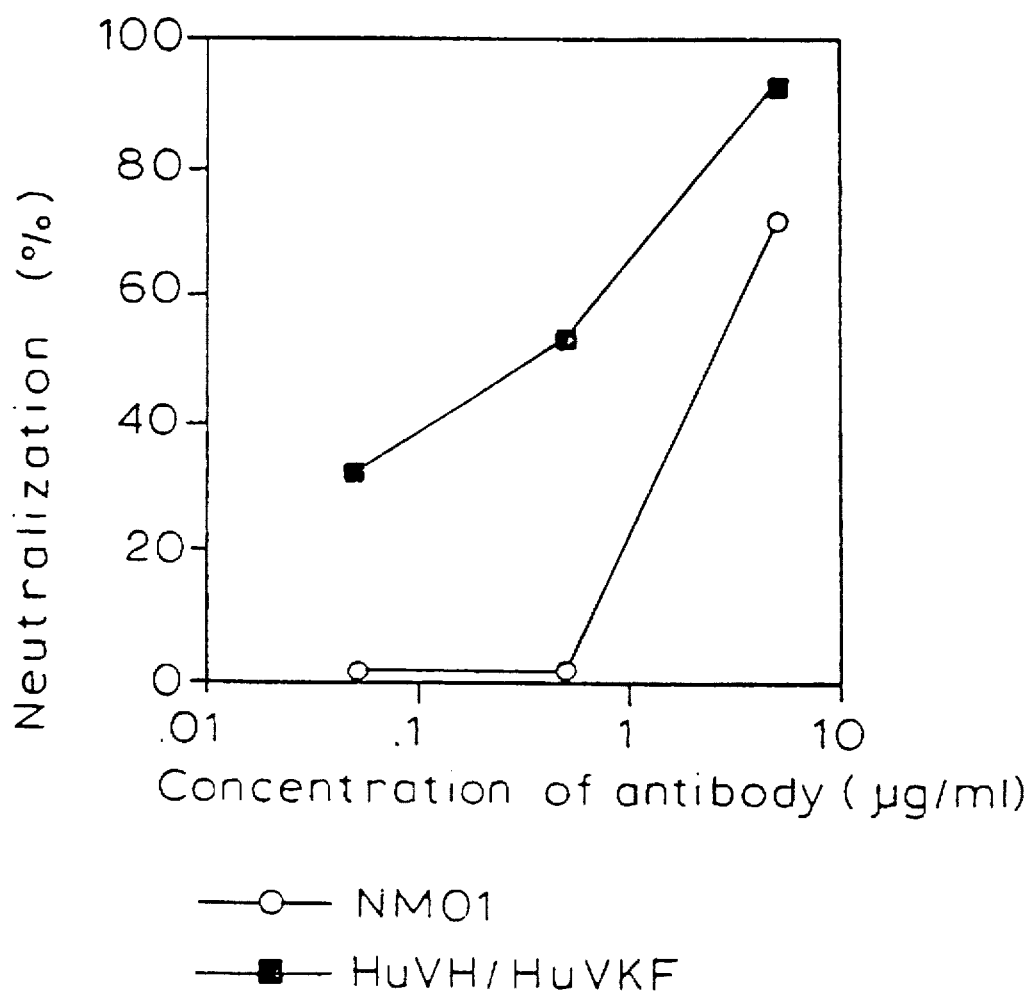
FIGS. 10 and 11 graphically illustrate neutralizing activity of antibodies NM-01 and HuVH/HuVKF against MN and $III_B$ strains of HIV-1 as determined by P24 assay.
Figure 11:
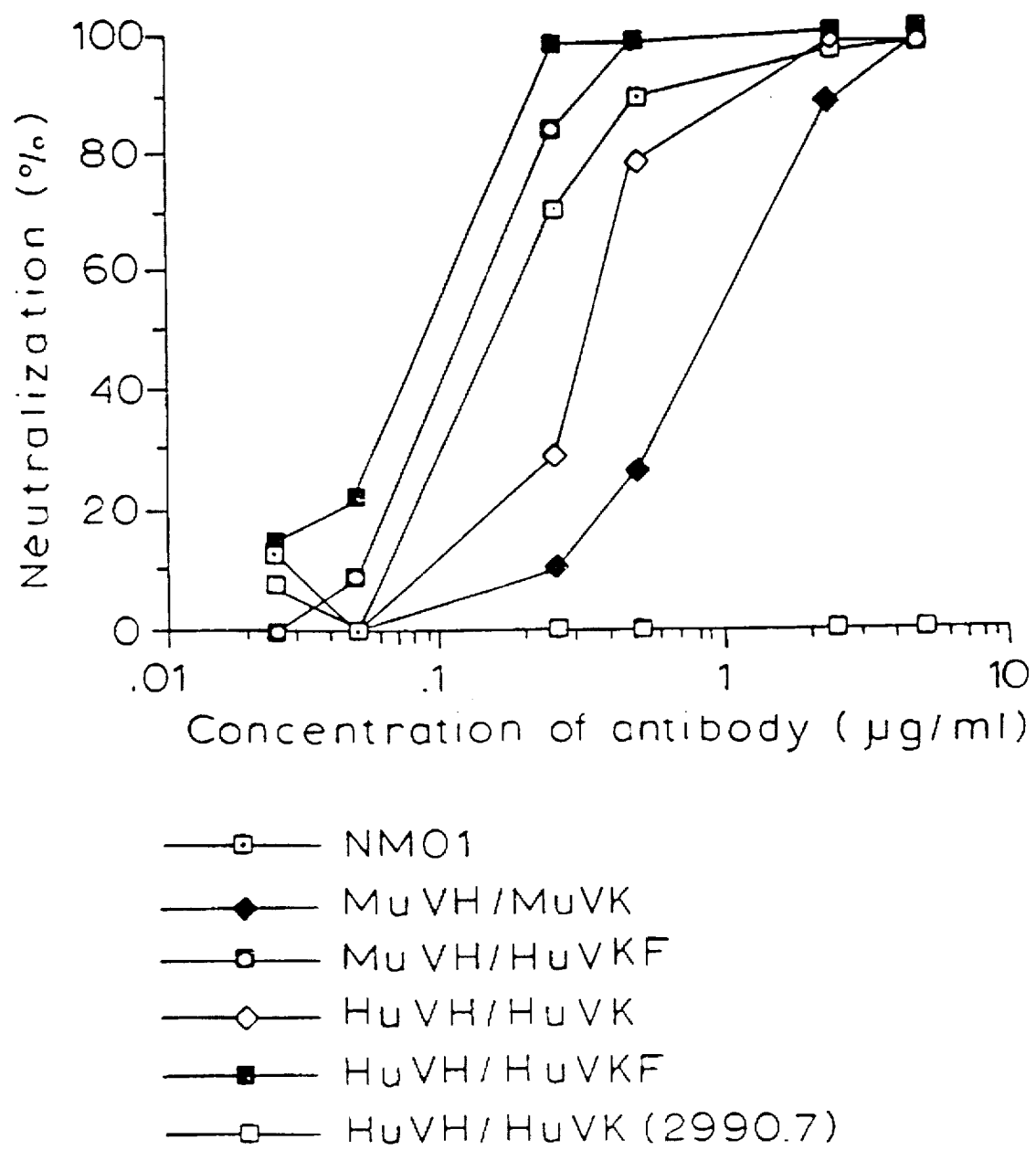

The antibodies were purified by protein A agarose affinity chromatography and tested for binding to recombinant gp120 as described in Example 2 (FIG. 3). The result indicates that the HuVH and MuVH chains are equivalent, as are the HuVK and MuVK chains with the HuVKF chain giving an advantage of 2–4 fold. This suggests that the NM-01 humanized antibodies (HuVH/HuVK and HuVH/HuVKF) bind well to recombinant gp120. The antibodies were similarly tested for their ability to bind to Triton X-100 lysate of MN virus and of a mutant MN virus (FIGS. 5A and 5B). The signal levels for the murine and recombinant antibodies cannot be compared as different reporter antibodies were used but the MuVH/MuVK, HuVH/HuVK and HuVH/HuVKF antibodies are all seen to bind to MN virus but not to a mutant virus to which NM-01 murine mAb will not bind.

Additional humanized antibody derivatives of NM-01 were also produced which also bound to recombinant gp120. The antibodies were produced by cell lines Hu VHS/Hu VKF G4, Hu VH/Hu VKF C4, Hu VHM/Hu VK G7, Hu VHM/Hu VKF G8, and Hu VHS/Hu VK F6. The antibodies comprise different heavy chains and previously described kappa chains as indicated in the name of the cell line. HuVHM is identical to HuVH except that the murine NM-01 residue M replaces I at Kabat position 48 (position 50 in FIG. 4A). HuVHS is identical to HuVH except that the murine NM-01 residue S replaces a at Kabat position 93 (position 98 in FIG. 4A).

Example 4

Determination of the NM-01 HuVH/HuVKF Epitope

The epitope of the humanized antibody NM-01 HuVH/HuVKF was investigated by peptide binding and competition ELISAs.

1. ELISA Against HIV-1 Peptide

Murine NM-01 binds to a loop peptide representing residues 312–326 of HIV-$1_{MN}$ gp120 which includes the GPGR motif.

The peptide (synthesised by Multiple Peptide Systems, San Diego, Calif., U.S.A.) and a negative control peptide, representing a different part of the V3 loop, (both 250 ng/100 μl 0.1 M sodium borate pH8.0 per well) were incubated overnight at 4° C. in Immulon 2 plates (Dynatech). The plates were washed with PBS-0.05% Tween 20 and blocked with PBS-0.1% Tween 20–0.1% BSA for 1h at room temperature. The blocking solution was removed, dilutions of NM-01 antibodies added in blocking solution and incubation continued at 37° C. for 1h. The plates were washed and HRPO-conjugated goat anti-mouse IgG antibodies (Zymed, San Francisco, Calif., U.S.A.; 60 ng/well) or HRPO-conjugated goat anti-human IgG antibodies (Sera-Lab Limited, Crawley Down, Sussex, UK; 40 ng/well) added. Following incubation at room temperature for 1h, the plates were washed and incubated in the presence of o-phenyldiamine until color had developed (about 5 min). Absorbances were read at 492 nm. The binding of the NM-01 antibodies to the HIV-$1_{MN}$gp120 residue 312–326 peptide is shown in FIG. 6; no binding was observed when the negative control peptide was used. The NM-01 HuVH/HuVKF antibody is seen to bind to the peptide with increased efficiency compared to the chimeric (MuVH/MuVK) antibody. Direct comparison to the murine NM-01 antibody cannot be made as different conjugated antibodies were used.

2. Blocking ELISA Against Recombinant gp120

Plates were coated with recombinant gp120 (5 ng/well) and blocked as described in Example 2. Dilutions of NM-01 antibodies or an irrelevant humanized antibody were added in 100 μl /well and the plates incubated at 37° C. for 30 min. Biotinylateed murine NM-01 antibody (500 mg/50 μl PBS, per well) was added and incubation continued for 1h. The plates were washed with PBS-0.05% Tween 20, HRPO-streptavidin (Sera-Lab Limited, Crawley Down, Sussex, UK, 40 ng/100 μl PBS, per well) added and incubation continued for 30 min. The plates were washed and incubated in the presence of o-phenyldiamine for 5 min. or until color developed. Absorbances were read at 492 nm.

The result is shown in FIG. 7 where direct comparison of the murine and recombinant NM-01 antibodies is possible. HuVH/HuVK is as efficient as the murine NM-01 in blocking the binding of labelled murine NM-01 antibody. The HuVH/HuVKF is approximately four-fold more active than the murine antibody whereas the chimeric (MuVH/MuVK) antibody is slightly deficient relative to the murine antibody -this is presumably due to the alterations made at the variable region terminus during creation of the chimeric antibody (Example 2). The irrelevant humanized antibody shows no blocking activity.

These two experiments show that the epitope recognised by the humanized NM-01 antibody, HuVH/HuVKF, is largely, if not completely, identical to that of the murine NM-01 antibody.

Example 5

Biological Activity of NM-01 HuVH/HuVKF

The humanized NM-01 antibody, HuVH/HuVKF, was compared with the murine NM-01 for capacity to neutralize infection of H9 cells by live HIV-1 strains MN and IIIB as measured by reverse transcriptase and p24 assays. The antibodies were also compared in a syncytium formation assay utilising live MN virus.

1. Reverse Transcriptase and p24 Assays

Dilutions of the antibodies were incubated with 100 $TCID_{50}$ of MN or $III_B$ live virus in 96-well plates for 2h at 4° C. H9 cells ($2.5\times105^5$) were then added to each well and the plates were incubated for another hour at 37° C. The H9 cell suspension was then diluted in 2 ml RPMI 1640/15% FBS and incubated in a 24 well plate at 37° C. Virus production was determined by reverse transcriptase (RT) assay performed on day 7 as described in Poiesz et al., *Proc. Natl. Acad. Sci, U.S.A.*, 77, pp. 7415–7419 (1980). The presence of p24 antigen in the tissue culture supernatant was quantitated after 6–8 days by the HIV-1 p24 core profile ELISA, using the method described by the manufacturer (Du Pont-New England Nuclear). Results are shown in FIGS. 8–12. With the MN strain, 50% neutralization of RT activity was achieved with 1.2 μg/ml murine NM-01 or 0.8 μg/ml NM-01 HuVH/HuVKF (FIG. 8). With strain $III_B$, the $ID_{50}$ was 0.2 μg/ml for murine NM-01 and 0.08 μg/ml for NM-01 HuVH/HuVKF (FIG. 9). By the p24 assay, 50% neutralization of MN virus required 1.5 μg/ml murine NM-01 or 0.3 μl/ml NM-01 HuVH/HuVKF (FIG. 10) and 50% neutralization of $III_B$ virus required 0.15 μg/ml murine NM-01 or 0.08 μg/ml NM-01 HuVH/HuVKF (FIG. 11). These results demonstrate that NM-01 HuVH/HuVKF is more effective in neutralizing NM and $III_B$ strains of HIV-1 than the parent murine NM-01. FIG. 11 also shows the neutralization activity of other recombinant NM-01 antibodies and an irrelevant humanized antibody (2990.7 HuVH/HuVK) which acts as a negative control. These results support that of the blocking ELISA which suggested the chimeric antibody (MuVH/MuVK) was deficient relative to the murine NM-01. The HuVH/HuVK antibody is again seen to be less efficient than the HuVH/HuVKF. The result with the mixed antibody MuVH/HuVKF indicates that the humanized kappa chain, rather than heavy chain, is responsible for the superior activity of HuVH/HuVKF compared to the murine antibody.

2. Syncytium Formation Assay

The binding inhibition assay was a modification of that described previously in Johnson and Walker, Eds., *Techniques in HIV-1 Research*, Stockton Press, New York, N.Y., pp. 92–97 (1990). Briefly, H9 cells chronically infected with MN virus were incubated with dilutions of the antibodies for 1h at 37° C. Cells from the indicator cell line C8166 were then added (3×10⁴ cells/well) and the plate incubated for 2–12h at 7° C. Syncytia greater than three lymphocyte cell diameters were counted and compared to that obtained for control infected H9 cells treated in the absence of antibody.

Figure 12:
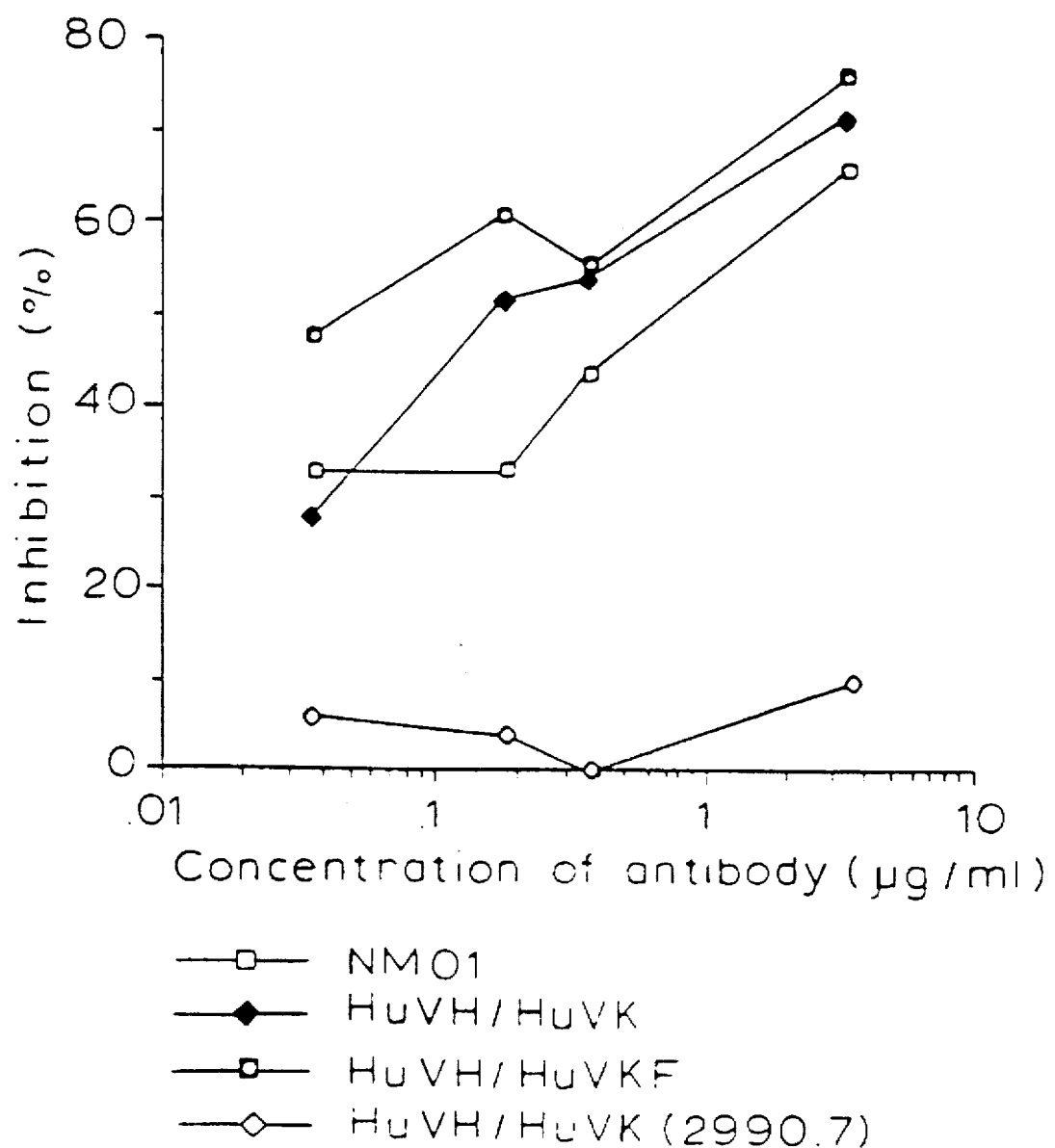
FIG. 12 shows the ability of the listed antibodies to inhibit syncytium formation by the MN strain of HIV-1.

The result is shown in FIG. 12 and demonstrates that an increased level of inhibition is achieved with the NM-01 HuVH/HuVKF antibody compared with the murine NM-01. The negative control humanized antibody (2990.7) had no detectable effect.

Example 6

Formulations

The humanized immunoglobulins of the subject invention and pharmaceutical compositions thereof are particularly useful for parenteral administration, e.g., subcutaneously intramuscularly or intravenously. The compositions for parenteral administration will typically comprise a solution of the humanized immunoglobulin dissolved in a physiologically acceptable carrier, preferably an aqueous carrier. A variety of aqueous carriers can be used, e.g., water, buffered water, physiological saline, 0.3% glycine, and the like. Solutions for parenteral administration are preferably sterile and generally free of particulate matter. Compositions for parenteral administration may be lyophilized for convenient storage and rehydrated prior to use. These compositions for parenteral administration may be sterilized by conventional sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate and the like. The concentration of humanized immunoglobulin in these formulations can vary widely, i.e., from less than about 0.5%, but usually at or at least about 1% to as much as 15% or 20% by weight and maybe selected primarily based on fluid volumes, viscosities, etc., in accordance with the particular mode of administration selected.

Example 7

Host Cells—Recombinant Production of Humanized Antibodies

Host cells may be cotransfected with the two expression vectors of the invention, the first vector containing an operon encoding a heavy chain derived polypeptide comprising a humanized heavy chain variable region and the second containing an operon encoding a light chain derived polypeptide comprising a humanized light chain variable region. The two vectors may contain different selectable markers but, with the exception of the heavy and light chain coding sequences, are preferably identical. This procedure provides for equal expression of heavy and light chain polypeptides. Alternatively, a single vector may be used which encodes both heavy and light chain polypeptides. The coding sequences for the heavy and light chains may comprise cDNA or genomic DNA or both.

The host cell used to express the recombinant antibody of the invention may be either a bacterial cell such as *Escherichia coli*, or preferably a eukaryotic cell. Preferably a mammalian cell, such as a myeloma cell line cell, may be used. The choice of expression vector is dependent upon the choice of host cell, and may be selected so as to have the desired expression and regulatory characteristics in the selected host cell.

The general methods for construction of the vector of the invention, transfection of cells to produce the host cell of the invention, and culture of cells to produce the antibody of the invention are all conventional molecular biology methods. Likewise, once produced, the recombinant antibodies of the invention may be purified by standard procedures of the art for the purification of antibodies and antibody derivatives, including cross-flow filtration, ammonium sulphate precipitation, affinity column chromatography, gel electrophoresis, and the like.

Example 8

Labeled Derivatives of Humanized Antibodies

The humanized HIV-1 gp120 specific antibodies of the present invention may be used in conjunction with, or attached to other antibodies (or parts thereof) such as human or humanized monoclonal antibodies. These other antibodies may be reactive with other markers (epitopes) characteristic for HIV-1 infections directly or may have different specificities chosen, for example, to recruit molecules or cells of the human immune system to HIV-1 infected cells. The antibodies of the invention (or parts thereof) may be administered with such antibodies (or parts thereof) as separately administered compositions or as a single composition with the two agents linked by conventional chemical or by molecular biological methods. Additionally the diagnostic and therapeutic value of the antibodies of the invention may be augmented by labelling the humanized antibodies with labels that produce a detectable signal (either in vitro or in vivo) or with a label having a therapeutic property. Some labels, e.g. radionuclides may produce a detectable signal and have a therapeutic property. Examples of radionuclide labels include $^{125}I$, $^{131}I$, $^{14}C$, $^{99}Tc$. Examples of other detectable labels include a fluorescent chromophore such as fluorescein, phycobiliprotein or tetraethyl rhodamine for fluorescence microscopy, an enzyme which produces a fluorescent or colored product for detection by fluorescence, absorbance, visible color or agglutination, which produces an electron dense product for demonstration by electron microscopy; or an electron dense molecule such as ferritin, peroxidase or gold beads for direct or indirect electron microscopic visualization. Labels having therapeutic properties include anti-viral drugs.

Example 9

Treatments of HIV Infections

The subject invention also provides for a variety of methods for treating, i.e., ameliorating, or preventing, i.e., prophylaxis, of HIV-1 infections. These methods involve the administration of humanized HIV-1 gp120 specific antibodies, either labelled or unlabelled, to a patient. In addition to administering humanized HIV-1 gp120 specific antibodies in the subject methods, the subject methods may also comprise the step of administering additional therapeutic compounds for the treatment or prevention of HIV-1 infections. Examples of such additional compounds include anti-viral drugs and antibodies (humanized or otherwise) specific for regions on a HIV-1 particle that are not bound by the humanized HIV-1 gp120 specific antibodies of the invention.

The precise dosage of humanized HIV-1 gp120 specific antibody administered to a patient for the treatment of prevention of a HIV-1 infection will vary in accordance with a number of factors appreciated by the typical clinician. Such factors include the size of the patient, the age of the patient, the general condition of the patient, the extent of the infection in the patient, the amount of HIV-1 in the patient, the presence of other drugs administered to the patient, method of administration, and the like. The development of a precise treatment regimen may require optimization through routine procedures well known to those of ordinary skill in the art in clinical medicine and pharmacokinetics. In general, a daily dose of between about 100 µg and about 5000 µg per Kg of patient body weight is contemplated.

Example 10

Neutralization of Infectious HIV

The subject invention also provides methods of removing or neutralizing infectious HIV-1 particles in a composition for administration to a patient, e.g., blood. The subject methods of removing/neutralizing infectious HIV-1 in a composition comprise the step of adding an effective concentration of humanized HIV-1 gp120 specific antibodies to the composition of interest. An effective amount for use in the neutralizing method is an amount at least equal to the suspected concentration of HIV-1 particles in the solution of interest, and is preferably at least an order of magnitude greater than the suspected amount of HIV-1 particles in the solution of interest. The use of humanized HIV-1 gp120-specific antibodies is particularly advantageous over comparable non-human antibodies because compositions, e.g., blood, treated with the HIV-1-neutralizing antibody may be administered to a patient with a decreased probability of causing an adverse immune reaction to non-human antibodies.

Example 11

HIV-1 Diagnostics

The subject invention also provides a variety of diagnostic methods for the detection of HIV-1 particles and HIV-1 infected cells. The subject humanized HIV-1 gp120-specific antibodies may be used for both in vivo and in vitro diagnostic techniques. These diagnostic methods employ well known immunodiagnostic techniques such as ELISA, Western blots, RIA, and the like, in which the HIV-1 specific antibody used for target recognition is a humanized HIV-1 gp120 antibody.

Biological Deposits

Prior to the filing of this application, applicants have deposited with the ECACC the following antibody producing cell lines as described herein: HuVHS/HuVKF G4 (accession # 93082018), HuVH/HuVKF C4 (accession # 93082019), HuVHM/HuVk G7 (accession #93082020), HuVHM/HuVKF G8 (accession # 93082021), Hu VHS/ HuVK F6 (accession # 93082023), and HuVH/HuVK F6 (accession # 93082022).

Availability of the deposited strain is not to be construed as a license to practice the invention in contravention of the rights granted under the authority of any government in accordance with its patent laws.

Equivalents

All publications and patents mentioned in the above specification are herein incorporated by reference. The foregoing written specification is considered to be sufficient to enable one skilled in the art to practice the invention. Indeed, various modifications of the above-described modes for carrying out the invention which are obvious to those skilled in the field of molecular biology or related fields are intended to be within the scope of the following claims.

We claim:

1. A humanized antibody produced by cell line HuVH/HuVKF C4 (E.C.A.C.C. Accession No. 93082019) having the same binding specificity as murine monoclonal NM-01 antibody produced by NM-01 hybridoma cell line (A.T.C.C. Accession No. HB 10726).

2. A polynucleotide encoding an antibody according to claim 1 and comprising the sequences for variable regions as set forth in SEQ ID NO: 8 SEQ ID NO: 10.

3. An expression vector comprising a polynucleotide according to claim 2 in functional combination with a promoter sequence.

4. A host cell transfected with an expression vector according to claim 3.

5. A host cell HuVH/HuVKF C4 (E.C.A.C.C. Accession No. 93082019) according to claim 4.

6. A method of producing a humanized antibody specific for HIV-1 gp120, said method comprising the steps of:

(a) culturing a host cell according to claim 4; and (b) isolating the humanized antibody.

* * * * *

UNITED STATES PATENT AND TRADEMARK OFFICE
CERTIFICATE OF CORRECTION

PATENT NO.   :   5,607,847                              Page 1 of 2
DATED        :   March 4, 1997
INVENTOR(S)  :   Harris et al.

It is certified that error appears in the above-identified patent and that said Letters Patent is hereby corrected as shown below:

Column 1, line 21 replace "in vivo" with "*in vivo*"

Column 2, line 47 replace "in vitro" with "*in vitro*"

Column 5, line 51 replace "HindIII" with "*Hind*III"

Column 5, line 51 replace "PstI" with "*Pst*I"

Column 5, line 65 replace "SalI" with "*Sal*I"

Column 5, line 66 replace "BamHI" with "*Bam*HI"

Column 6, line 12 replace "HindIII-PvuII" with "*Hind*III-*Pvu*II"

Column 6, line 13 replace "HindIII-SalI" with "*Hind*III-*Sal*I"

Column 6, line 57 replace "Me" with "MA"

Column 6. line 60 replace "PstI" with "*Pst*I"

Column 6, line 61 replace "BstEII" with "*Bst*EII"

Column 6, line 62 replace "PvuII" with "*Pvu*II"

Column 6, line 62 replace "BclI" with "*Bcl*I"

UNITED STATES PATENT AND TRADEMARK OFFICE
CERTIFICATE OF CORRECTION

PATENT NO. : 5,607,847

DATED : March 4, 1997

INVENTOR(S) : Harris et al.

It is certified that error appears in the above-identified patent and that said Letters Patent is hereby corrected as shown below:

Column 6, lines 63-64 replace "PvuII-BqIII" with "PvuII-BqIII"

Col. 7, line 8, replace "HindIII-BamHI" with "HindIII-BamHI"

Col. 7, line 9, replace "BamHI" with "BamHI"

Column 7, line 29 replace "Me" with "MA"

Column 7, line 41 replace "o" with "o"

Column 9, line 18 replace "replaces a at" with "replace A at"

Column 10, line 29 replace "(2.5x105⁶)" with "(2.5x10⁶)"

Signed and Sealed this

Fourth Day of November, 1997

BRUCE LEHMAN

*Attest:*

*Attesting Officer*   *Commissioner of Patents and Trademarks*

SEQUENCE LISTING ( 1 ) GENERAL INFORMATION:

( i i i ) NUMBER OF SEQUENCES: 16

( 2 ) INFORMATION FOR SEQ ID NO: 1:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA primer ( x i ) SEQUENCE DESCRIPTION: SEQ ID NO: 1:

GGAAGCTTAG ACCGATGGGG CTGTTGTTTT G        31

( 2 ) INFORMATION FOR SEQ ID NO: 2:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA primer ( x i ) SEQUENCE DESCRIPTION: SEQ ID NO: 2:

GGAAGCTTGA AGATGGATAC AGTTGGTGCA GC        32

( 2 ) INFORMATION FOR SEQ ID NO: 3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA primer ( x i ) SEQUENCE DESCRIPTION: SEQ ID NO: 3:

AGGTSMARCT GCAGSAGTCW GG                      22

( 2 ) INFORMATION FOR SEQ ID NO: 4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA primer ( x i ) SEQUENCE DESCRIPTION: SEQ ID NO: 4:

GACATTCAGC TGACCCAGTC TCCA                    24

( 2 ) INFORMATION FOR SEQ ID NO: 5:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA primer ( x i ) SEQUENCE DESCRIPTION: SEQ ID NO: 5:

TGAGGAGACG GTGACCGTGG TCCCTTGGCC CCAG          34

( 2 ) INFORMATION FOR SEQ ID NO: 6:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA primer ( x i ) SEQUENCE DESCRIPTION: SEQ ID NO: 6:

TTGTCGACAT GATGGTGTTA AGTCTTCTGT ACCTG         35

( 2 ) INFORMATION FOR SEQ ID NO: 7:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA primer ( x i ) SEQUENCE DESCRIPTION: SEQ ID NO: 7:

AAGTCGACAT GRRTWTASTC ACWCACCTSC TRKSGKT      37

( 2 ) INFORMATION FOR SEQ ID NO: 8:

( i ) SEQUENCE CHARACTERISTICS:
        ( A ) LENGTH: 363 base pairs
        ( B ) TYPE: nucleic acid 5,607,847

17

-continued ( C ) STRANDEDNESS: double
( D ) TOPOLOGY: linear ( i i ) MOLECULE TYPE: cDNA to mRNA ( x i ) SEQUENCE DESCRIPTION: SEQ ID NO: 8:

| | | | | | |
|---|---|---|---|---|---|
| CAGATTCAGC | TTAAGGAGTC | TGGACCTGCT | GTCATCAAGC | CATCACAGTC | ACTGTCTCTC | 60 |
| ACCTGCATAG | TCTCTGGATT | CTCCATCACA | AGTAGTAGTT | ATTGCTGGCA | CTGGATCCGC | 120 |
| CAGCCCCCAG | GAAAGGGGTT | AGAGTGGATG | GGGCGCATAT | GTTATGAAGG | TTCAATAGAC | 180 |
| TATAGTCCAT | CCATCAAAAG | CCGCAGCACC | ATCTCCAGAG | ACACATCTCT | GAACAGATTC | 240 |
| TTTATCCAGC | TGAGTTCTGT | GACAAATGAG | GACACTGCCA | TGTATTACTG | TTCCAGGGAA | 300 |
| AACCATGGTA | CTACGACCTC | TATGGACTAC | TGGGGTCAAG | GAACCTCAGT | CACCGTCTCC | 360 |
| TCA | | | | | | 363 |

( 2 ) INFORMATION FOR SEQ ID NO: 9:

( i ) SEQUENCE CHARACTERISTICS:
( A ) LENGTH: 121 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO: 9:

Gln Ile Gln Leu Lys Glu Ser Gly Pro Ala Val Ile Lys Pro Ser Gln
1               5                   10                  15

Ser Leu Ser Leu Thr Cys Ile Val Ser Gly Phe Ser Ile Thr Ser Ser
            20                  25                  30

Ser Tyr Cys Trp His Trp Ile Arg Gln Pro Pro Gly Lys Gly Leu Glu
        35                  40                  45

Trp Met Gly Arg Ile Cys Tyr Glu Gly Ser Ile Asp Tyr Ser Pro Ser
    50                  55                  60

Ile Lys Ser Arg Ser Thr Ile Ser Arg Asp Thr Ser Leu Asn Arg Phe
65                  70                  75                  80

Phe Ile Gln Leu Ser Ser Val Thr Asn Glu Asp Thr Ala Met Tyr Tyr
                85                  90                  95

Cys Ser Arg Glu Asn His Gly Thr Thr Thr Ser Met Asp Tyr Trp Gly
            100                 105                 110

Gln Gly Thr Ser Val Thr Val Ser Ser
        115                 120

( 2 ) INFORMATION FOR SEQ ID NO: 10:

( i ) SEQUENCE CHARACTERISTICS:
( A ) LENGTH: 333 base pairs
( B ) TYPE: nucleic acid
( C ) STRANDEDNESS: double
( D ) TOPOLOGY: linear ( i i ) MOLECULE TYPE: cDNA to mRNA ( x i ) SEQUENCE DESCRIPTION: SEQ ID NO: 10:

| | | | | | |
|---|---|---|---|---|---|
| GACATTGTGC | TGACCCAGTC | TCCAGCTTCT | TTGGCTGTGT | CTCTAGGGCA | GAGGGCCACC | 60 |
| ATATCCTGCA | GAGCCAGTGA | AAGTGTTGAT | AGTTATGGCA | ATAGTTTTAT | GCACTGGTAC | 120 |
| CAGCAGAAAC | CAGGACAGTC | ACCCAAACTC | CTCATCTATG | TTGCATCCAA | CCTAGAATCT | 180 |
| GGGGTCCCTG | CCAGGTTCAG | TGGCAGTGGG | TCTAGGACAG | ACTTCACCCT | CACCATTGAT | 240 |
| CCTGTGGAGG | CTGATGATGC | TGCAACCTAT | TACTGTCAGC | AAAATAATGA | GGATCCGCTC | 300 |

ACGTTCGGTG CTGGGACCAA GCTGGAGCTG AAA    333

(2) INFORMATION FOR SEQ ID NO: 11:

(i) SEQUENCE CHARACTERISTICS:
        (A) LENGTH: 111 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 11:

```
Asp Ile Val Leu Thr Gln Ser Pro Ala Ser Leu Ala Val Ser Leu Gly
 1               5                  10                  15
Gln Arg Ala Thr Ile Ser Cys Arg Ala Ser Glu Ser Val Asp Ser Tyr
            20                  25                  30
Gly Asn Ser Phe Met His Trp Tyr Gln Gln Lys Pro Gly Gln Ser Pro
            35                  40                  45
Lys Leu Leu Ile Tyr Val Ala Ser Asn Leu Glu Ser Gly Val Pro Ala
        50                  55                  60
Arg Phe Ser Gly Ser Gly Ser Arg Thr Asp Phe Thr Leu Thr Ile Asp
65                  70                  75                  80
Pro Val Glu Ala Asp Asp Ala Ala Thr Tyr Tyr Cys Gln Gln Asn Asn
                85                  90                  95
Glu Asp Pro Leu Thr Phe Gly Ala Gly Thr Lys Leu Glu Leu Lys
                100                 105                 110
```

(2) INFORMATION FOR SEQ ID NO: 12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO: 12:

GTTAGATCTC CAGCTTGGTC CC    22

(2) INFORMATION FOR SEQ ID NO: 13:

(i) SEQUENCE CHARACTERISTICS:
        (A) LENGTH: 121 amino acids
        (B) TYPE: amino acid
        (D) TOPOLOGY: linear (ii) MOLECULE TYPE: protein (xi) SEQUENCE DESCRIPTION: SEQ ID NO: 13:

```
Gln Val Gln Leu Gln Glu Ser Gly Pro Gly Leu Val Arg Pro Ser Gln
 1               5                  10                  15
Thr Leu Ser Leu Thr Cys Thr Val Ser Gly Phe Ser Ile Thr Ser Ser
            20                  25                  30
Ser Tyr Cys Trp His Trp Val Arg Gln Pro Pro Gly Arg Gly Leu Glu
            35                  40                  45
Trp Ile Gly Arg Ile Cys Tyr Glu Gly Ser Ile Asp Tyr Ser Pro Ser
        50                  55                  60
Ile Lys Ser Arg Val Thr Met Leu Arg Asp Thr Ser Lys Asn Gln Phe
65                  70                  75                  80
Ser Leu Arg Leu Ser Ser Val Thr Ala Ala Asp Thr Ala Val Tyr Tyr
```

|   |   |   | 85 |   |   |   |   | 90 |   |   |   |   | 95 |   |   |
|---|---|---|---|---|---|---|---|---|---|---|---|---|---|---|---|
| Cys | Ala | Arg | Glu | Asn | His | Gly | Thr | Thr | Thr | Ser | Met | Asp | Tyr | Trp | Gly |
|   |   |   | 100 |   |   |   |   | 105 |   |   |   |   | 110 |   |   |
| Gln | Gly | Ser | Leu | Val | Thr | Val | Ser | Ser |   |   |   |   |   |   |   |
|   |   |   | 115 |   |   |   | 120 |   |   |   |   |   |   |   |   |

( 2 ) INFORMATION FOR SEQ ID NO: 14:

( i ) SEQUENCE CHARACTERISTICS:
        ( A ) LENGTH: 111 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 14:

| Asp | Ile | Gln | Met | Thr | Gln | Ser | Pro | Ser | Ser | Leu | Ser | Ala | Ser | Val | Gly |
|---|---|---|---|---|---|---|---|---|---|---|---|---|---|---|---|
| 1 |   |   |   | 5 |   |   |   |   | 10 |   |   |   |   | 15 |   |
| Asp | Arg | Val | Thr | Ile | Thr | Cys | Arg | Ala | Ser | Glu | Ser | Val | Asp | Ser | Tyr |
|   |   |   | 20 |   |   |   |   | 25 |   |   |   |   | 30 |   |   |
| Gly | Asn | Ser | Phe | Met | His | Trp | Tyr | Gln | Gln | Thr | Pro | Gly | Lys | Ala | Pro |
|   |   | 35 |   |   |   |   | 40 |   |   |   |   | 45 |   |   |   |
| Lys | Leu | Leu | Ile | Tyr | Val | Ala | Ser | Asn | Leu | Glu | Ser | Gly | Val | Pro | Ser |
|   | 50 |   |   |   |   | 55 |   |   |   |   | 60 |   |   |   |   |
| Arg | Phe | Ser | Gly | Ser | Gly | Ser | Gly | Thr | Asp | Tyr | Thr | Phe | Thr | Ile | Ser |
| 65 |   |   |   |   | 70 |   |   |   |   | 75 |   |   |   |   | 80 |
| Ser | Leu | Gln | Pro | Glu | Asp | Ile | Ala | Thr | Tyr | Tyr | Cys | Gln | Gln | Asn | Asn |
|   |   |   |   | 85 |   |   |   |   | 90 |   |   |   |   | 95 |   |
| Glu | Asp | Pro | Leu | Thr | Phe | Gly | Gln | Gly | Thr | Lys | Leu | Gln | Ile | Thr |   |
|   |   |   | 100 |   |   |   |   | 105 |   |   |   |   | 110 |   |   |

( 2 ) INFORMATION FOR SEQ ID NO: 15:

( i ) SEQUENCE CHARACTERISTICS:
        ( A ) LENGTH: 363 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO: 15:

| TGAGGAGACG | GTGACTGAGG | TTCCTTGACC | CCAGTAGTCC | ATAGAGGTCG | TAGTACCATG | 60 |
| GTTTTCCCTG | GAACAGTAAT | ACATGGCAGT | GTCCTCATTT | GTCACAGAAC | TCAGCTGGAT | 120 |
| AAAGAATCTG | TTCAGAGATG | TGTCTCTGGA | GATGGTGCTG | CGGCTTTTGA | TGGATGGACT | 180 |
| ATAGTCTATT | GAACCTTCAT | AACATATGCG | CCCCATCCAC | TCTAACCCCT | TTCCTGGGGG | 240 |
| CTGGCGGATC | CAGTGCCAGC | AATAACTACT | ACTTGTGATG | GAGAATCCAG | AGACTATGCA | 300 |
| GGTGAGAGAC | AGTGACTGTG | ATGGCTTGAT | GACAGCAGGT | CCAGACTCCT | TAAGCTGAAT | 360 |
| CTG |   |   |   |   |   | 363 |

( 2 ) INFORMATION FOR SEQ ID NO: 16:

( i ) SEQUENCE CHARACTERISTICS:
        ( A ) LENGTH: 333 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO: 16:

-continued

| | | | | | | |
|---|---|---|---|---|---|---|
| TTTCAGCTCC | AGCTTGGTCC | CAGCACCGAA | CGTGAGCGGA | TCCTCATTAT | TTTGCTGACA | 60 |
| GTAATAGGTT | GCAGCATCAT | CAGCCTCCAC | AGGATCAATG | GTGAGGGTGA | AGTCTGTCCT | 120 |
| AGACCCACTG | CCACTGAACC | TGGCAGGGAC | CCCAGATTCT | AGGTTGGATG | CAACATAGAT | 180 |
| GAGGAGTTTG | GGTGACTGTC | CTGGTTTCTG | CTGGTACCAG | TGCATAAAAC | TATTGCCATA | 240 |
| ACTATCAACA | CTTTCACTGG | CTCTGCAGGA | TATGGTGGCC | CTCTGCCCTA | GAGACACAGC | 300 |
| CAAAGAAGCT | GGAGACTGGG | TCAGCACAAT | GTC | | | 333 |